United States Patent
Bousseljot et al.

(10) Patent No.: US 6,607,480 B1
(45) Date of Patent: Aug. 19, 2003

(54) EVALUATION SYSTEM FOR OBTAINING DIAGNOSTIC INFORMATION FROM THE SIGNALS AND DATA OF MEDICAL SENSOR SYSTEMS

(75) Inventors: Ralf Bousseljot, Königs Wusterhausen (DE); Dieter Kreiseler, Berlin (DE)

(73) Assignee: Federal Republic of Germany, Braunschwieg (DE)

( * ) Notice: Subject to any disclaimer, the term of this patent is extended or adjusted under 35 U.S.C. 154(b) by 0 days.

(21) Appl. No.: 09/623,346

(22) PCT Filed: Mar. 4, 1998

(86) PCT No.: PCT/DE98/00625
§ 371 (c)(1),
(2), (4) Date: Sep. 1, 2000

(87) PCT Pub. No.: WO99/44498
PCT Pub. Date: Sep. 10, 1999

(51) Int. Cl.$^7$ .................................................. A61N 5/00
(52) U.S. Cl. ........................................................ 600/300
(58) Field of Search ............................... 600/300–301, 600/505, 515; 128/920–925

(56) References Cited

U.S. PATENT DOCUMENTS

| | | | |
|---|---|---|---|
| 4,930,075 A | | 5/1990 | Kortas |
| 5,020,540 A | | 6/1991 | Chamoun |
| 5,022,404 A | | 6/1991 | Hafner |
| 5,025,794 A | | 6/1991 | Albert et al. |
| 5,029,082 A | | 7/1991 | Shen et al. |
| 5,159,932 A | | 11/1992 | Zanetti et al. |
| 5,217,012 A | | 6/1993 | Young et al. |
| 5,240,009 A | | 8/1993 | Williams |
| 5,259,387 A | | 11/1993 | dePinto |
| 5,277,189 A | * | 1/1994 | Jacobs ........................ 600/505 |
| 5,280,792 A | | 1/1994 | Leong et al. |
| 5,341,811 A | | 8/1994 | Cano |
| 5,355,891 A | | 10/1994 | Wateridge et al. |
| 5,355,892 A | | 10/1994 | Saltzstein et al. |
| 5,357,969 A | | 10/1994 | Herleikson |
| 5,542,429 A | * | 8/1996 | Feng ........................... 600/515 |
| 6,050,940 A | * | 4/2000 | Braun et al. ................ 600/300 |
| 6,306,077 B1 | * | 10/2001 | Prabhu et al. ................ 600/26 |
| 6,338,713 B1 | * | 1/2002 | Chamoun et al. ........... 600/300 |

* cited by examiner

Primary Examiner—Max F. Hindenburg
(74) Attorney, Agent, or Firm—Husch & Eppenberger, LLC; Robert E. Muir; David A. Chambers

(57) ABSTRACT

The invention provides a means of deriving highly reliable diagnostic information from the signals and data of medical measuring systems without first reducing the measuring data to individual characteristics and then associating these using decision trees in order to form a diagnostic conclusion. To this end, a comparator compares the measuring data recorded by a patient and provided by the sensor channels of a measuring system with measuring data which is stored in measuring databases and which is provided by comparable sensor channels of reference measuring systems. The data is compared in such a way that the reference measuring systems selected from the measuring databases are those which bear the most similarity to the measurements taken by the patient in terms of the measuring data of comparable sensor channels and which have a greatest possible number of the sensor channels which best match in terms of measuring data and which best correspond to each other. The selected reference measuring systems, along with the information belonging to the reference measuring systems of the measuring database and the comparison of this with the information belonging to the patient, are then used to form a diagnostic conclusion which applies to the patient with a certain degree of probability.

10 Claims, 5 Drawing Sheets

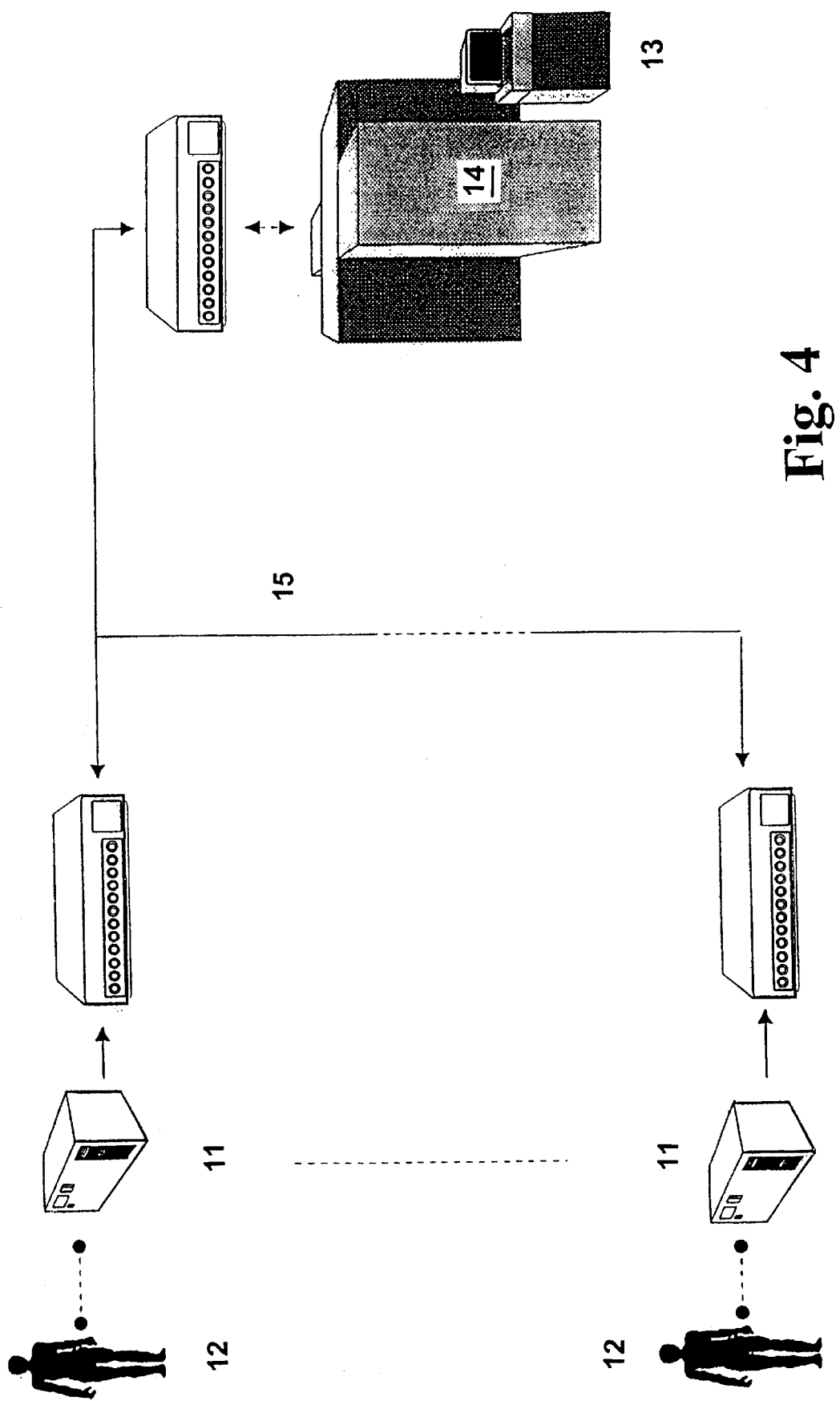

Figure 1:
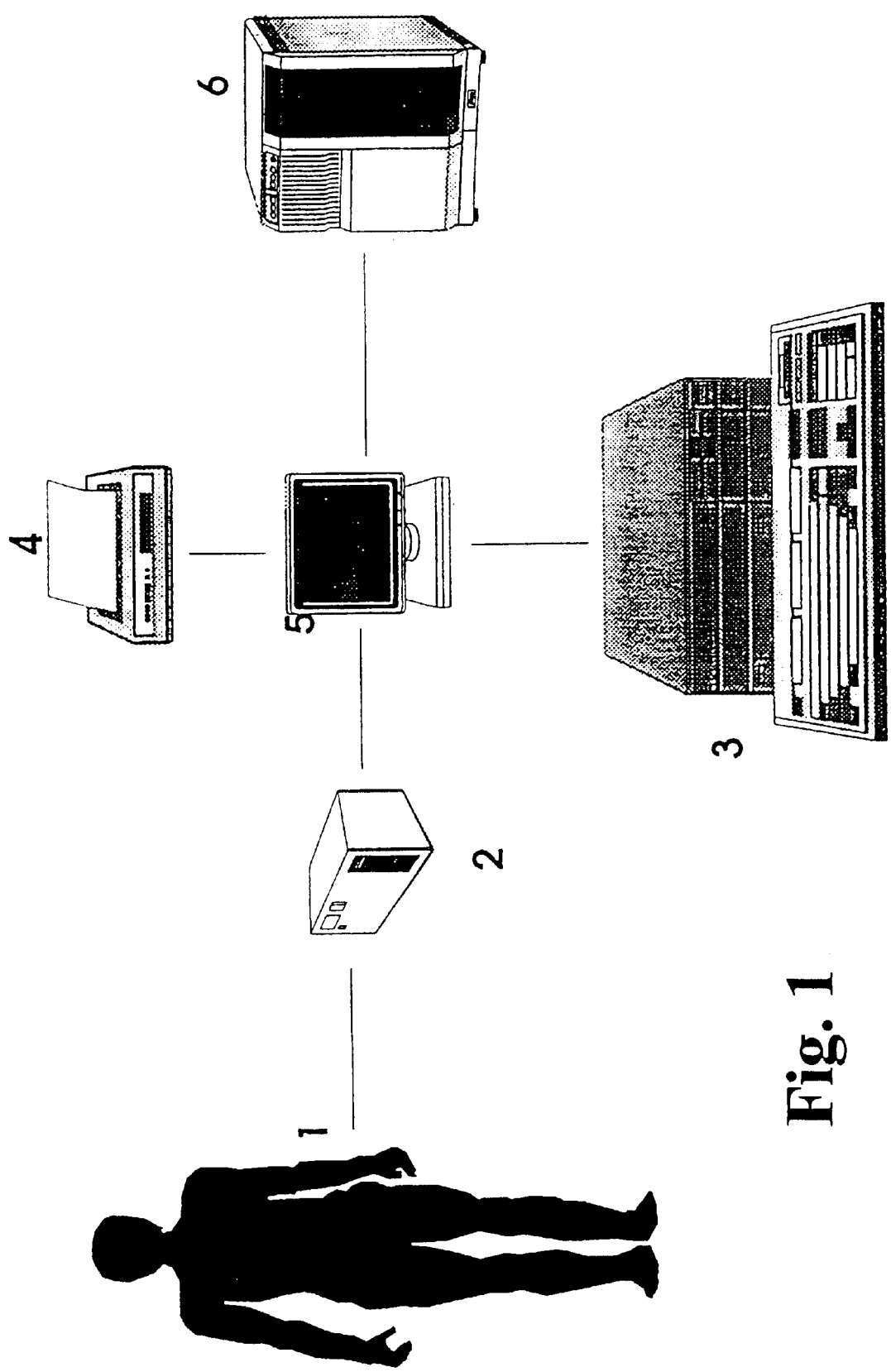

EVALUATION SYSTEM FOR OBTAINING DIAGNOSTIC INFORMATION FROM THE SIGNALS AND DATA OF MEDICAL SENSOR SYSTEMS

FIELD OF APPLICATION OF THE INVENTION

The invention relates generally to the field of medical diagnostics, and more particularly to an evaluating system for obtaining diagnostic information from signals and data of medical sensor systems by means of measurement data and patient databases.

CHARACTERISTICS OF KNOWN TECHNICAL SOLUTIONS

To an increasing extent in medical diagnosis use is made of systems which obtain diagnostic information from signals and data derived from the patient. This group of systems also includes the automatically evaluating electrocardiographs (EKG apparatus).

EKG evaluating systems, e.g. according to U.S. Pat. No. 5,022,404, detect one or more electrode potentials of electrodes attached to the patient, and filter and digitalized them. Then these signals are fed via a multiplexer to a microcomputer with CPU, work memory, etc. existing in the EKG evaluating system. The computer processes the measured signals, e.g. by removal of the baseline drift according to DE 41 06 856, U.S. Pat. No. 5,357,969 or the removal of muscle artefacts from the EKG according to U.S. Pat. No. 5,259,387. Moreover, it calculates the medical derivations necessary for medical analysis of the EKG according to Wilson, Goldberg, Einthoven and/or the orthogonal derivations according to Frank. At its simplest these medical derivations are either shown on paper strips and/or electronic displays, e.g. in U.S. Pat. No. 5,022,404 on LCDs, and evaluated by the doctor doing the evaluation. More intelligent, so-called evaluating electrocardiographs use the microcomputer existing in the apparatus for, apart from signal processing and display, also signal evaluation, signal measurement and, if occasion arises, for the output of diagnostic information such as e.g. in U.S. Pat. No. 5,029,082.

Signal measurement and evaluation are effected, as described in patents of which more details are given below, as a rule in such a way that from the calculated medical derivations are determined a number of individual signal parameters important for cardiological assessment of the EKG with respect to time and amplitude or criteria derived therefrom. A problem with this determination of individual signal parameters is the different approaches, such as e.g. in exact determination of the zero line of the EKG for determining the starting point of the P wave and the resulting determination of the duration of the P wave, which deliver quite substantially differing results depending on the quality of the method used. The patents are amongst others DE 43 10 412 (evaluation of the ST segment or other T wave), DE 39 27 709 (evaluation of the ST section), U.S. Pat. No. 5,159,932 (filtering of the EKG, QRS finding, averaging) or U.S. Pat. No. 5,020,540 (analysis of the frequency structure of the QRST complex, waveform template). Further relevant patents contain determination of individual parameters of the EKG, or serve to detect limited diagnostic information, e.g. in U.S. Pat. No. 4,930,075 (evaluation of the ST segment for the detection of ischemias), U.S. Pat. No. 5,025,794 (method of bidirectional filtering for the detection of retarded potentials), U.S. Pat. No. 5,355,891 (automatic signal averaging by beat triggering for the detection of retarded potentials), U.S. Pat. No. 5,341,811 (HP filtering of at least two channels, weigh adaptive filters for common-mode rejection, retarded potential detection) or DE43 04 269 (evaluation of the ST section for the assessment of acute ischemic damage).

The signal parameters determined are printed out on the paper strip or indicated directly together with the signal path of the EKG. For the output of diagnostic information, in a more or less complicated branched decision tree the individual signal parameters determined are linked together into meaningful diagnostic information. This is done for example by the many programs forming the basis of computer EKG apparatus. Such decision trees can have for example the following form: "If parameter 1 occurs in conjunction with parameter 3 and/or parameter 4 and in medical derivation a at the same time condition 1 is operative, from this can be inferred the diagnostic information xyz". In this way for every known diagnosis a decision tree can be built up on the basis of individual signal parameters determined from the EKG in its derivations. This method is extremely elaborate on account of the large number of influencing variables and parameters and requires extensive cardiological knowledge or experience. Changes or improvements in the methods for determining individual parameters, control of empirically determined threshold values or new medical knowledge require sometimes elaborate program alterations and function tests and are therefore associated with high costs or require new EKG apparatus with the revised programs. The patent U.S. Pat. No. 5,355,892 therefore describes an EKG system with portable storage media (floppy disk drive) for the storage of both EKG and patient information, e.g. for hospital information systems, as well as for reloading or updating algorithms for EKG evaluation.

A more recent group of EKG apparatus or methods try to obtain limited diagnostic information from the EKG signal by means of adaptive neuronal networks such as e.g. DE 43 07 545 (multi-channel measurement of electrical and/or magnetic field variables at least during part of the heart cycle, evaluations with an adaptive classifier (neuronal network for the classification and location of ischemias and/or infarctions) or U.S. Pat. No. 5,280,792 (arrhythmia classification by means of a combination of time analysis and sample comparison as well as neuronal networks). A problem with these methods is both the high learning effort in training the neuronal networks and the fact that neuronal networks are themselves at the stage of applied basic research. A full analysis of an EKG with the aim of deriving complex diagnostic information requires, on account of the complexity of an EKG, a very high number of neurons or, associated with this, a very high computing capacity.

A further group of EKG apparatus or methods serves for the analysis and diagnosis of rhythm disturbances, e.g. for cardiac pacemakers or direct control of defibrillators. These include e.g. patents DE 32 09 850 (classification of rhythm disturbances, evaluation by comparison of the complete curve of the EKG with EKG curves of the patient under examination detected or calculated previously in a learning phase, full storage of an example of the EKG curve for each class of rhythm disturbances of the patient under examination), U.S. Pat. No. 5,240,009 (detection of rhythm disturbances by comparison of averaged and stored waveform complexes with current complexes of the same patient), U.S. Pat. No. 5,217,012 (correlation of result-free portions of own EKG with areas of the EKG with rhythm disturbances, compression and storage of the result-free EKG areas, alarm criterion is exceeding the threshold value of cross-correlation function) or DE 43 20 519

(measurement and comparison of three heartbeat periods and then of at least fifty heartbeat curves, diagnosis of heart rhythm disturbances). A common feature of all these methods is that in each case they test only certain diagnostic groups or given individual features of the EKG.

AIM OF THE INVENTION

The invention makes it possible to derive diagnostic information with high reliability from recorded signals and data of electrical and/or magnetic medical measurement systems, without reducing the measurement data initially to more or less complex individual characteristics which depend on the progress of knowledge, and then linking these individual characteristics by means of decision tress or neural networks which are difficult to modify, into diagnostic information.

It is the object of the invention to make the obtaining of diagnostic information from the measurement data of medical measurement systems, such as EKG systems, largely independent of the more or less complex evaluation of individual characteristics, which change constantly with the progress of knowledge, and decision trees based on those characteristics or the comprehensive process of training neural networks. According to the invention the object is achieved by the fact that a comparator compares measurement data of a patient from one or more sensor channels with all or some of the measurement data of comparable sensor channels of reference measurements stored in one or more measurement databases and selects the reference measurements which have the greatest similarity to the patient's measurement with respect to the measurement data of comparable sensor channels and also a maximum possible number of sensor channels which match most in the measurement data and correspond to each other. A probability is also inferred from a comparison of the technical, medical, diagnostic and personal information belonging to the reference measurements of the measurement database and the patients' diagnostic information.

PRACTICAL EXAMPLE

Figure 1A:
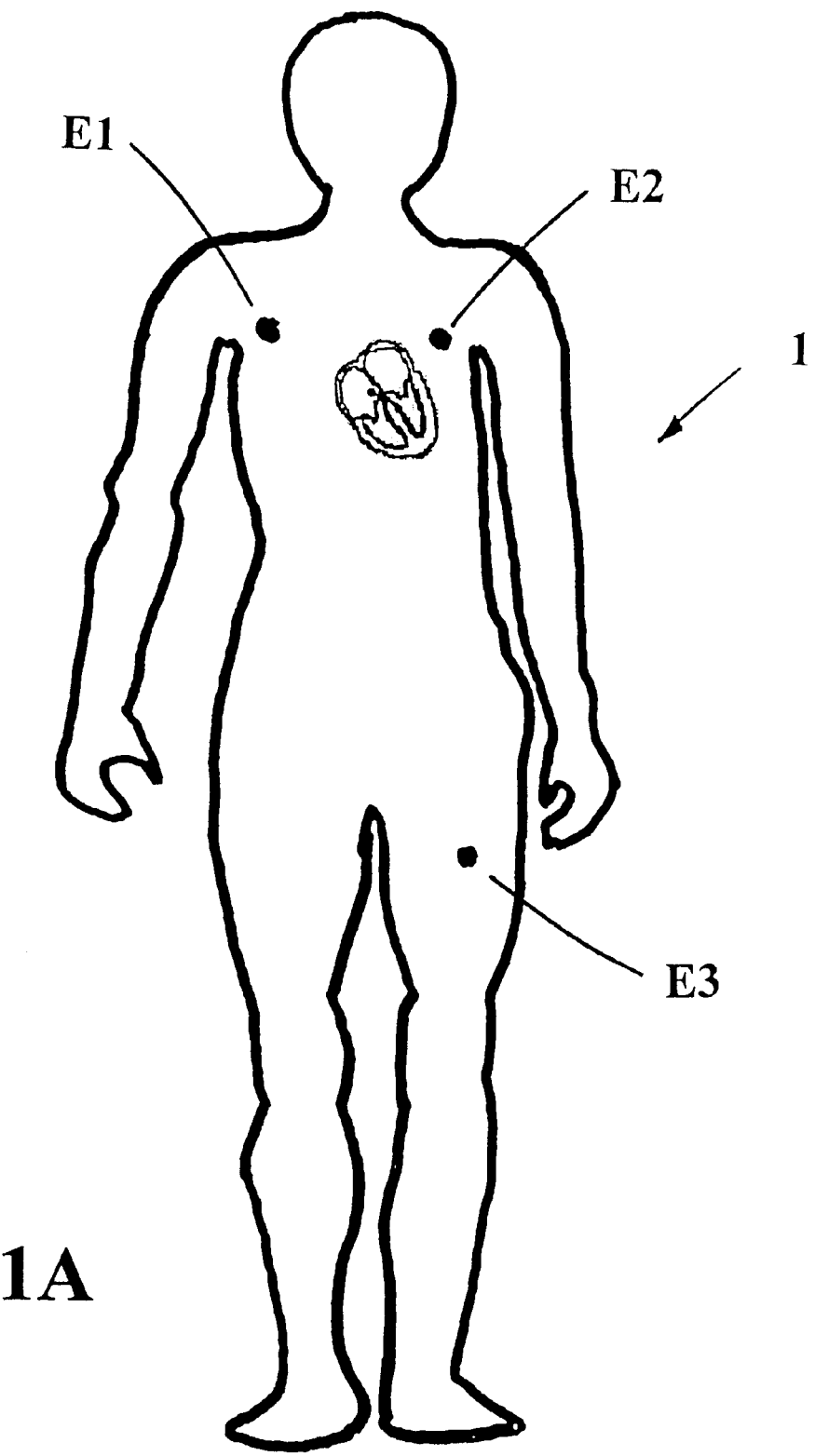
Figure 2:
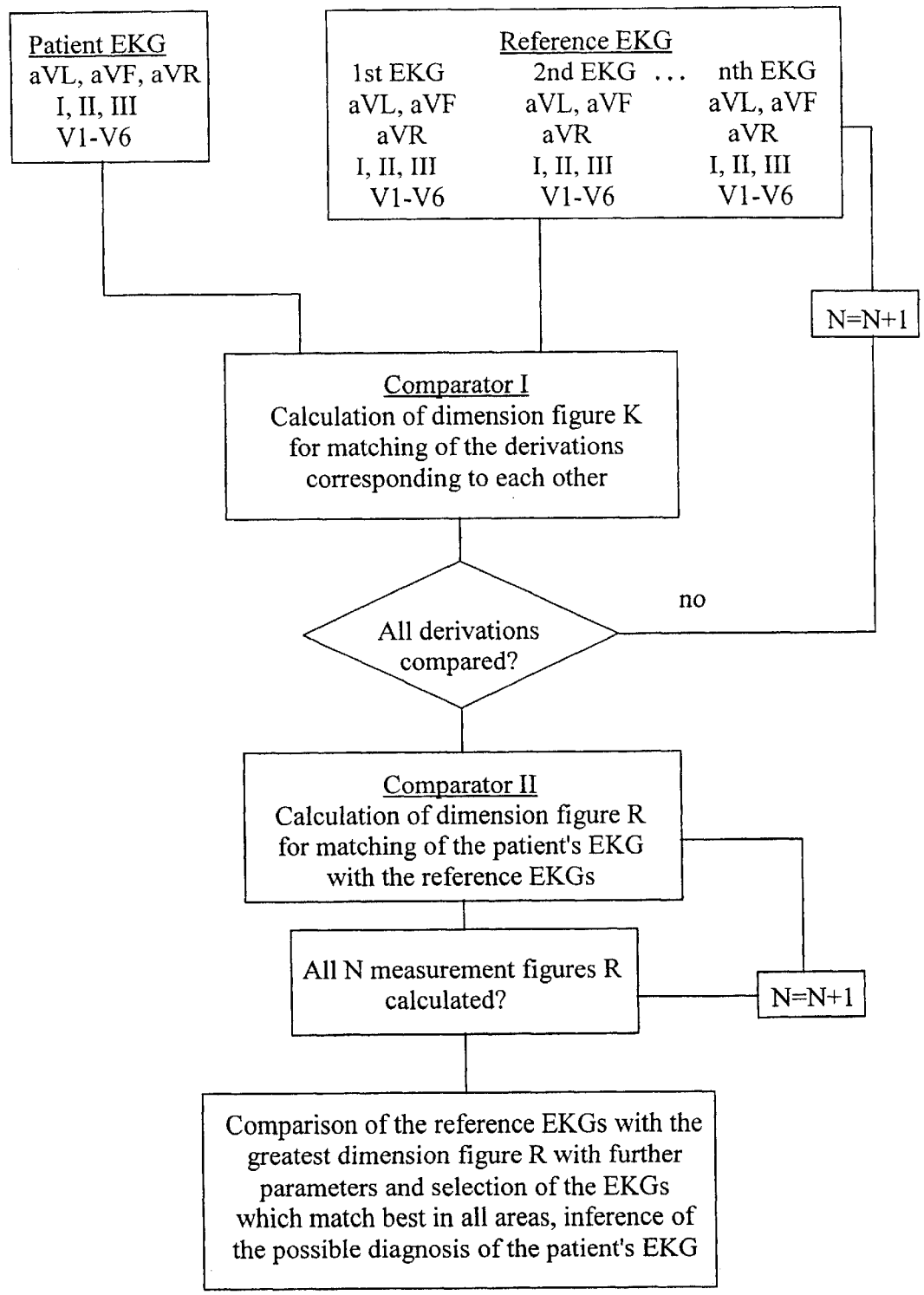
Figure 3:
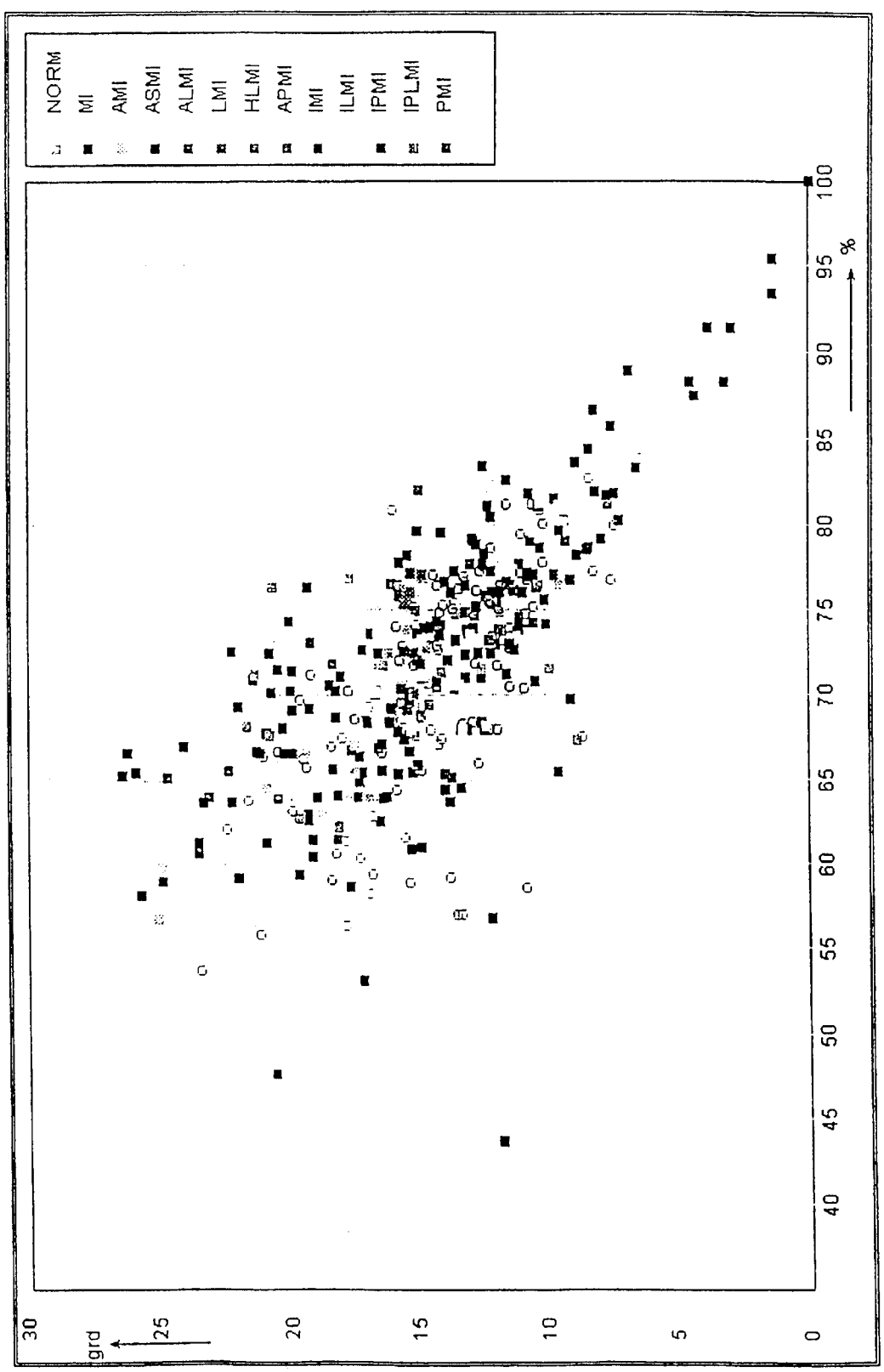

The invention will be described in more detail below by two practical examples. The associated drawings show:

FIG. 1: is a basic drawing of a local EKG recording system with a database on CD-ROM;

FIG. 1A: is a representation of a patient showing the location of some standard electrodes;

FIG. 2: is a schematic drawing of the function of an example of the comparator for deriving diagnostic information from the processed measurement data;

FIG. 3: is a representation of the result of an evaluation of an EKG in relation to 370 EKG of a signal database (cardiac infarctions); and FIG. 4: is a basic drawing of an EKG recording system with a network-based SQL database and network-based evaluation.

FIG. 1 illustrates a local EKG recording and evaluating system. Electrodes (E1–E3, etc.) attached to a patient (1) in the usual manner are shown in FIG. 1A. A right leg electrode (not shown) is used as the ground. In clinical practice, twelve leads are usually used in a diagnostic EKG, although there is no limitation to the number one may select for special purposes. Hence the showing of three electrodes (E1–E3) is illustrative. The electrical potentials of the patient's heart are detected and amplified, filtered and digitized by a measurement processing system (2). A microcomputer (3) calculates medical derivations from these processed measurement signals according to 12-channel standard derivations. The medical derivations are stored in their relationship as an EKG measurement and, if occasion arises, outputted via a printer (4) or displayed on a monitor (5). A database is stored on one or more CD-ROMs which are located in a CD-ROM system (6) connected to the microcomputer (3). The database contains EKG measurements recorded at an earlier time as well as further information on these EKG measurements. The database may be stored on CD-ROMs or other suitable electronic mass storage means. The EKG signals of the reference measurements stored in the database also occur in the present embodiment as 12-channel standard derivations. Here the bandwidth of the digitized EKG signals contained in the database according to the Nyquist theory corresponds to not more than half the scan rate of the EKG signals recorded with the EKG recording and evaluating system. For each patient contained in the database, several EKG recordings can be stored at given time intervals in the present example. The other information stored in the database includes patient-related information, information on anamnesis, test results, laboratory values, medical diagnoses, information on the nature of the patient's treatment, drugs administered, etc. A comparator (see FIG. 2) compares a patient's EKG measurement derivations with EKG derivations of reference measurements stored in one or more measurement databases and selects the reference measurements which have the greatest similarity to the measurement recorded by the patient with respect to the measurement data of comparable sensor channels and also a maximum possible number of sensor channels which match in the measurement data and correspond to each other. By comparing the medical, diagnostic and personal information belonging to the reference measurements of the measurement database, diagnostic information which applies to the patient can be inferred with a certain probability. The comparator can also be designed completely or partially as a hardware circuit to save computing time. The basic progress of evaluation is shown in more detail in FIG. 2. In the example for this purpose in a first step the individual medical derivations aVL, aVR, aVF, V1–V6, I, II, III of the 12-channel standard derivation are compared with the comparable medical derivations stored in the database with respect to matching of their signal patterns. For example, the derivation V1 of the patient is compared with the derivations V1 contained in the database, and a dimension figure $K_{11}$ to $K_{1n}$ is calculated for the degree of matching of derivation V1 with the derivations $V1_n$ of the n reference EKGs of the database. The same is repeated for each medical derivation so that in the example for each compared EKG of the database there are twelve measurement figures $K_{1n}$ to $K_{12n}$ (taking 12 derivations into consideration) for the degree of matching of the respective comparable derivations.

These twelve measurement figures for each EKG are compiled into a dimension figure R which describes matching of the recorded EKG with each EKG stored in the database in its derivations.

The EKGs with the greatest matching in all their derivations, which show the highest degree of matching of their signal patterns, are selected. The EKGs best matching the patient's measurements are selected from these EKGs with respect to further information contained in the database. FIG. 3 illustrates one possible result of this selection process for cardiac infarctions in a two-dimensional drawing showing the degree of matching of the unknown patient EKG with the known data bank EKGs. The closer a database EKG is placed to the bottom right corner, the greater its matching with the FKG of the patient. More extensive differentiation of the selection in the case of several data bank EKGs which match the patient EKG well, can be obtained by assigning the diagnostic information contained in the database to that of the patient.

An essential advantage of the solution according to the invention is the possibility of improving the reliability of detection of EKG analysis systems by simply extending the number of EKGs and associated reference information contained in the database, by reflecting the natural biological variability in a more representative fashion and so increasing the probability of finding one or more EKGs in the database similar to the patient's EKG.

FIG. 4 describes another possible embodiment. The electrical potentials of a patient's heart field are measured, filtered and digitized by an EKG sensor system (11) having sensors at certain points of the upper torso of the patient (12), the sensor system being connected to a network. A database (3) with measurement signals of comparable EKG measurements together with further information belonging to the measurement signals, so-called reference measurements, are located on a powerful computer system (14) which is installed at a central location and connected to a network. Both the EKG sensor system and the computer system (14) containing the database are connected to each other by a local or worldwide network (15) of sufficient transmission capacity. This network (15) can be formed by a LAN in a hospital or by telephone lines, ISDN dialing lines or the Internet.

The measurement data together with other particulars relating to the patient (12) are transmitted by the EKG measurement processing system (11) in a first step via the network (15) to the computer system (14) with the connected database (13). The computer system (14), as already described in more detail for example in FIG. 2, selects the EKGs of the database (13) which have the maximum possible matching both in their individual medical derivations and in the entirety of their measurement, and for which there is maximum possible matching between patient and database with respect to further particulars. Following evaluation by the computer system (14), the results of the comparison are transmitted back via the network (15) to the EKG measurement processing system (11) and indicated at the location of the EKG sensor system or outputted in suitable form or fed directly to corresponding hospital information systems.

Advantages of this solution lie in the possibility of building up a substantially more powerful computer system (14) at a central location with a substantially larger and more complex database than would be possible in local EKG apparatus with conventional evaluation. This leads to more precise information on the EKG to be evaluated, as it depends only on the quality of the database, i.e. the number of EKG measurements stored and their matching with the possible biological diversity of cardiological results. Furthermore with suitable efficiency both of the network (15), the central computer (14) and the database (13), several EKG sensor systems can be operated at the same time. Moreover, in this way the costs of the EKG recording system can be reduced, because the latter does not have to contain its own diagnostic evaluation or its own database.

If such a system is installed for example in a cardiological hospital with very high EKG yields, then at a suitable moment, for example at the end of the patient's treatment, his EKG signals and other personal information can be added to the database, thereby enhancing the database. This results in a knowledge base which represents biological diversity better and better.

What is claimed is:

1. An evaluating system for obtaining diagnostic information for a current patient from signals of medical systems, including:

a medical sensor system having a plurality of sensor channels for detecting biological activities of a patient over a given period of time and outputting corresponding sensor signals;

at least one database containing a plurality of reference data sets, each reference data set including comparable sensor signals and technical, medical, diagnostic and personal information for a past patient;

a comparator in communication with the medical sensor system and the database which compares the sensor signals with the comparable sensor channels of the reference data sets stored in the database, wherein the comparator selects reference data sets having similar sensor signals to the sensor signals of the current patient; and a computer which determines a probability for the selected reference data sets by comparing the technical, medical, diagnostic and personal information of the selected reference data sets with technical, medical, diagnostic and personal information from the current patient.

2. An evaluating system for obtaining diagnostic information from signals of medical systems according to claim 1, wherein the sensor channels provide a continuous sequence of sensor signals over a given period of time and one or more segments of limited time from this continuous sequence of measured values.

3. An evaluating system for obtaining diagnostic information from signals of medical systems according to claim 1, wherein each reference data set in the database also contains additional personal information of the past patient which is used by the comparator to further adjust the probability of the reference data set.

4. An evaluating system for obtaining diagnostic information from signals of medical systems according to claim 1, wherein the database contains reference data sets having sensor signals and technical, medical, diagnostic and personal information from both healthy persons and sick persons.

5. An evaluating system for obtaining diagnostic information from signals of medical systems according to claim 1, wherein new reference data sets are added to the database.

6. An evaluating system for obtaining diagnostic information from signals of medical systems according to claim 1, including an electronic storage medium on which the database is stored.

7. An evaluating system for obtaining diagnostic information from signals of medical systems according to claim 1, wherein the medical sensor system further includes biological sensor systems in communication with the sensor channels which are attached to the patient.

8. An evaluating system for obtaining diagnostic information from signals of medical systems according to claim 1, wherein the medical sensor system is an electrocardiograph recording system.

9. An evaluating system for obtaining diagnostic information from signals of medical sensor systems according to claim 1, including an electronic storage medium located remotely from the recording system and on which the database is stored, and a data network by which the database is available.

10. An evaluating system for obtaining diagnostic information from signals and data of medical sensor systems according to claim 1, wherein the medical sensor system is a cardiological recording system.

* * * * *